United States Patent
Muhl et al.

(10) Patent No.: US 8,287,182 B2
(45) Date of Patent: Oct. 16, 2012

(54) METHOD FOR TESTING A FRYING OIL TESTER

(75) Inventors: Mike Muhl, Freiburg (DE); Juergen Hall, Roetenbach (DE); Markus Langenbacher, Schluchsee (DE)

(73) Assignee: Testo AG, Lenzkirch (DE)

( * ) Notice: Subject to any disclaimer, the term of this patent is extended or adjusted under 35 U.S.C. 154(b) by 517 days.

(21) Appl. No.: 12/223,200

(22) PCT Filed: Jan. 24, 2007

(86) PCT No.: PCT/EP2007/000573
§ 371 (c)(1),
(2), (4) Date: Mar. 18, 2010

(87) PCT Pub. No.: WO2007/085426
PCT Pub. Date: Aug. 2, 2007

(65) Prior Publication Data
US 2010/0172391 A1 Jul. 8, 2010

(30) Foreign Application Priority Data
Jan. 26, 2006 (DE) .......................... 10 2006 003 733

(51) Int. Cl.
*G01K 15/00* (2006.01)
*G01N 33/03* (2006.01)
(52) U.S. Cl. .................. 374/1; 374/45; 324/698
(58) Field of Classification Search .............. 374/1, 45; 324/698
See application file for complete search history.

(56) References Cited

U.S. PATENT DOCUMENTS

| | | | | |
|---|---|---|---|---|
| 3,753,092 | A | * | 8/1973 | Ludlow et al. ............... 324/663 |
| 4,949,469 | A | * | 8/1990 | Wachtler ........................ 33/702 |
| 5,818,731 | A | | 10/1998 | Mittal et al. |
| 5,887,978 | A | | 3/1999 | Lunghofer et al. |
| 6,469,521 | B1 | * | 10/2002 | Klun et al. .................... 324/658 |
| 7,523,006 | B2 | * | 4/2009 | Muhl et al. ..................... 702/52 |
| 7,628,531 | B2 | * | 12/2009 | Lee et al. .......................... 374/1 |
| 7,652,490 | B2 | * | 1/2010 | Muhl et al. .................... 324/691 |
| 7,719,289 | B2 | * | 5/2010 | Muhl et al. .................... 324/658 |
| 2008/0238445 | A1 | * | 10/2008 | Muhl et al. .................... 324/663 |
| 2010/0116022 | A1 | * | 5/2010 | Cummings ................... 73/23.41 |
| 2011/0030486 | A1 | * | 2/2011 | Hall et al. ....................... 73/866 |
| 2012/0140789 | A1 | * | 6/2012 | Colburn et al. ................... 374/1 |

FOREIGN PATENT DOCUMENTS

| | | |
|---|---|---|
| DE | 102 02 002 A1 | 8/2003 |
| DE | 20 2005 007 144 U1 | 8/2005 |
| DE | 10 2004 012 420 A1 | 9/2005 |
| WO | WO 2000/40939 | 7/2000 |

OTHER PUBLICATIONS

"Changes in Dielectric Constant as a Measure of Frying Oil Deterioration", Fritsch, et al., General Mills, Inc., XP008080427, Journal of the American Oil Chemists' Society, pp. 746-750, vol. 56, Aug. 1979.

* cited by examiner

*Primary Examiner* — Christopher Fulton
(74) *Attorney, Agent, or Firm* — Muirhead and Saturnelli, LLC

(57) ABSTRACT

A method for testing a measuring device is used to determine a permittivity of a frying fat which permittivity is inter alia dependent on the temperature, while taking into consideration the temperature. The method is characterized in that the permittivity is measured at least two different temperatures and the temperature dependence is determined and is used to make a statement on the ability to function of the measuring device.

20 Claims, 1 Drawing Sheet

METHOD FOR TESTING A FRYING OIL TESTER

TECHNICAL FIELD

This application relates to a method for testing a measuring device, which ascertains a physical variable dependent, inter alia, on the temperature of a studied object under consideration of the measured temperature.

BACKGROUND OF THE INVENTION

Measuring devices which are operated in commercial use are typically checked occasionally or regularly and may be readjusted and/or recalibrated as needed. This may be performed, for example, in that a reference measurement is performed on a studied object whose physical variable to be measured is known, so that a measured value may be compared to a setpoint value. A further calibrated measuring device may also be used for a comparison measurement.

A physical variable of this type may, for example, be a dielectric constant (permittivity) of an organic material, which is often used in food technology for checking the age status of a food (e.g., frying oil), for example. The dielectric constant is then a function on the one hand of the age of the studied object, and on the other hand of the temperature. In known measuring devices, the temperature is measured and the measurement of the dielectric constant is standardized to room temperature using a temperature characteristics field for this reason.

Accordingly, it would be desirable to provide a simplified method for testing a measuring device of the type cited at the beginning.

SUMMARY OF THE INVENTION

According to an embodiment of the system described herein, a physical variable to be measured of a studied object may be measured at least two different temperatures and it may then be ascertained how well the measuring device is sufficiently and well calibrated on the basis of the temperature dependence of the measurement known for different values of the physical variable to be measured.

By measuring the physical variable at different temperatures, the temperature behavior of the physical variable is first determined. This temperature behavior actually differs for different values of the physical variable. Either temperature-corrected measurements are performed at different temperatures and it is checked whether the temperature correction results in comparable measured values of the physical variable to be measured, or a temperature characteristic—in the simplest case a straight line with two measured values—is recorded for the physical variable to be measured without temperature correction. It is established by comparison to a stored temperature characteristics field or by a mathematical analysis using corresponding known distinctive numbers for the temperature behavior whether the ascertained temperature behavior corresponds to an actually known temperature behavior at any conceivable value of the physical variable. In other words, a characteristic which fits the ascertained temperature behavior is picked out from the temperature characteristics field. If this is successful, it is simultaneously known at which actually existing value the physical variable fits the existing temperature characteristic and it is thus known which setpoint value of the physical variable to be measured is to be displayed by the measuring device. If this value does not correspond to the actual value of the physical variable, a recalibration is necessary. This may already be performed on site on the basis of the analysis if needed. A signal is then given to the user of the measuring device that he must perform a calibration (or have one performed).

If the ascertained temperature behavior does not correspond to a possible temperature behavior, it is also to be established that a calibration of the measuring device must occur. Maximum values are stored for the deviation of the ascertained temperature behavior from stored possible temperature characteristics, which causes a warning signal to be output if they are exceeded in the course of the method according to the system described herein.

An advantage of the testing method according to the system described herein is that the actual value of the physical variable to be measured does not have to be known during the testing of the measuring device. It may be analyzed on the basis of the coupling of the temperature dependence to the physical variable whether or not the ascertained temperature dependence fits with the displayed value of the physical variable within the scope of a permitted imprecision.

This advantage, which is achieved by the system described herein, helps ensure that corresponding tests may be performed on site by the user of the measuring device with the reduced effort.

For this purpose, only temperature characteristics for the physical variables to be measured have to be stored in the measuring device in the form of graphs or in the form of few parameters which describe the corresponding graphs. For example, if a linear dependence exists, only the slope of the temperature curve and an offset may be stored as the parameters.

In an embodiment of the method according to the system described herein, the variable to be measured is measured multiple times during a heating or cooling process of the studied object.

Heating or cooling of this type often occurs in practice in any case with the studied objects, so that the method may be performed without greater effort. Measurements may also be performed at more than two temperatures for more precise detection of the temperature dependence.

It may also be provided that an actually existing value of the physical variable is assigned to the temperature dependence of the physical variable to be measured which is ascertained by measuring without temperature compensation, that this actually existing value is compared to the measured value of the physical variable, and that a signal is output if a minimum deviation exists.

It may also be provided that the temperature dependence of the physical variable is ascertained on the basis of measurements, that the actual value of the physical variable of the studied object is known, and that both the measurement of the physical variable and the consideration of the temperature dependence are calibrated on the basis of these data. The user may not only learn on site whether a calibration is necessary, but rather may also at least perform a crude calibration himself, without the measuring device having to be checked in a laboratory.

For a more precise calibration, it may also be provided that reference measurements of the physical variable are performed at two known values of the physical variable and that measurements of the temperature dependence occur at each of two different values of the physical variable, that a calibration in regard to the measurement of the physical variable and in regard to the consideration of the temperature dependence is performed on the basis of the acquired data.

On the one hand the measurement of the physical variable to be measured is calibrated and on the other hand the temperature characteristics field and its assignment to the various values of the physical variable are adjusted by this method.

In another embodiment of the method according to the system described herein, for a known temperature and two different studied objects, for each of which the physical variable to be measured is known, this variable is measured and that the measurement is calibrated on the basis of the temperature dependence known for different values of the variable to be measured.

The fact is also exploited in this method that a coupling exists between the temperature measurement and the physical variable to be measured. This variant is a quasi-mathematical reversed application of the method according to the system described herein, in that a characteristics field of the physical variable is presumed for a fixed temperature and it is checked by measuring the variable on two different studied objects whether the consideration of the temperature dependence must be readjusted.

A complete and optimized calibration of the measuring device is performed in that a test measurement is performed at two known values of the physical variable to be measured and a measurement is performed at two different temperatures for each of these measured points. This so-called four-point measurement allows a calibration of the entire characteristics field.

The system described herein may advantageously be applied if the physical variable to be measured is the permittivity or a physical variable clearly connected thereto, such as a relative dielectric constant, an index of refraction, the capacitance of a capacitor, or a similar variable.

The system described herein may be provided for measuring objects whose permittivity may change, in particular frying fat or oil, in which the permittivity changes with age and/or use. The measured permittivity is thus a variable from which the age status may be determined. The method according to the system described herein thus allows a rapid and simple method for the function test in a frying oil tester. In the area of application of a frying oil tester, there are no easily available reference liquids which are stable both at high temperatures and also in the long-term and may be used as a reference for a function test in commercial use. The method according to the system described herein allows the function test even without a reference liquid, in that a measurement is performed at two different temperatures of a frying fat. This may be performed during heating or cooling of the deep fryer or during a regulation cycle of the temperature, if the hysteresis during the regulation permits appropriately high temperature differences, as are required for the precision of the measurement. An automatic check of a measuring device during heating or cooling may thus also occur with stationary systems.

After the check, depending on the measurement result, the device may either show a green light in a display, which means that the measuring device is still adequately calibrated, or an indication, for example, by a red light, that recalibration is necessary. A recalibration of this type may be performed at least crudely on site according to the method described above. In addition, however, a further factory calibration may also be performed if needed. The operating costs for corresponding measuring devices are thus decreased significantly by the system described herein.

BRIEF DESCRIPTION OF THE DRAWINGS

Embodiments of the system described herein are explained hereafter in reference to the figures of the drawings, briefly described as follows.

DETAILED DESCRIPTION OF VARIOUS EMBODIMENTS

Figure 1:
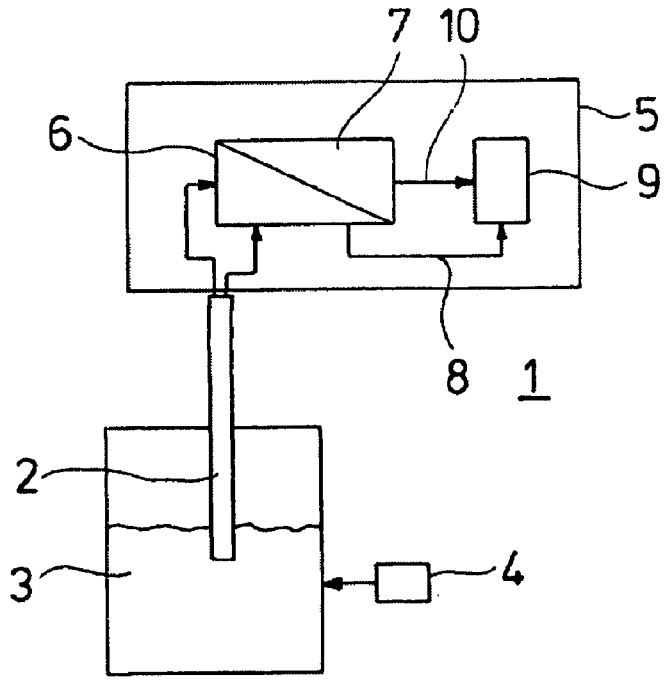
FIG. 1 schematically shows a measuring device which may be checked according to an embodiment of the system described herein.

FIG. 1 shows a measuring device 1 having a measuring head 2, which is immersed in a frying fat 3. The temperature of frying fat 3 is influenced using a regulating unit 4.

Sensors for measuring the temperature and the permittivity of frying oil 3 are provided at the end of measuring head 2. The corresponding measured values, provided in schematically shown analysis part 5 of measuring device 1, are supplied to a first analysis module 6, which performs a temperature compensation of the measured permittivity on the basis of the measured temperature and a temperature characteristics field stored in a memory 7. The corresponding measurement result is supplied according to arrow 8 shown in the figure to a display unit 9 of the measuring device and displayed there as a corrected measured value.

During a test or calibration of the measuring device, frying fat 3 is brought to two different temperatures using temperature regulation unit 4 and the permittivity and the temperature are measured in each case. This may also be performed in a similar way during cooling of the fat. On the basis of the various measured permittivities and the temperatures, the temperature dependence of the permittivity is ascertained in analysis module 6 and it is established whether the temperature behavior is sufficiently well corrected or, in the event of a non-temperature-corrected measurement, the temperature behavior is compared to temperature curves for various actual permittivities stored in memory 7. If the ascertained temperature dependence does not fit with the temperature characteristics field, the command is given to the display unit as indicated by arrow 10 to output a signal that the measuring device no longer functions reliably enough. If the measured temperature dependence corresponds to a curve from the characteristics field, it may be concluded therefrom that the value of the permittivity to which the corresponding stored curve belongs actually exists. This value may be compared to the measured value of the permittivity and either compensated for by readjusting the measuring device or, if they do not correspond, it may also be indicated by display unit 9 that the measuring device is no longer functionally reliable and recalibration should take place.

Figure 2:
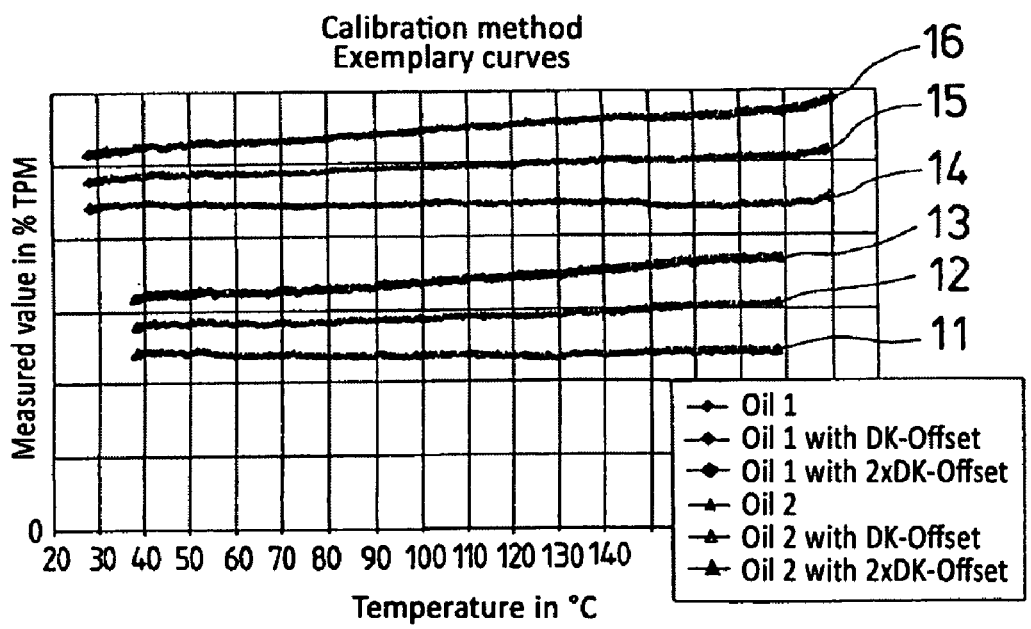
FIG. 2 shows a characteristics field of the temperature dependence for various values of a dielectric constant to be measured according to an embodiment of the system described herein.

FIG. 2 shows a corresponding curve family with the dependence of the permittivity, plotted against the y axis, and/or the value % tpm corresponding thereto, which corresponds to the age status of a frying fat, on the temperature, plotted against the x axis, in degrees Celsius for various permittivity values. It is apparent that different temperature dependences of the permittivity exist in each case in curves 11 through 16.

Therefore, upon measurement of the corresponding temperature dependence curves, which may be approximated as straight lines in a first approximation, for example, a conclusion may be drawn about the actually existing value of the permittivity and/or about an incorrect display due to an offset of the permittivity value based on the adjustment.

For example, curve 11 shows a well-calibrated measuring device in which the same permittivity value is displayed over the entire temperature range between 40° C. and 180° C. due to the temperature compensation. If an offset of the permittivity value is set (curve 12), the temperature compensation no longer functions optimally, and this has the result that the measured permittivity is no longer corrected for the entire temperature range. This allows a maladjustment to be concluded. This defect is further reinforced by an increased offset, as shown in curve 13.

If the permittivity is measured temperature-compensated at two temperature values, a maladjustment in the permittivity measurement may be concluded from a difference of the measured values and/or from the slope of the curve, if one exists. In the simplest case, the slope of the curve may thus be determined by the two measurements and a warning signal may be output if the curve slope exceeds a threshold value.

Curves 14, 15, 16 show the same effect for a second frying oil, lowermost curve 14 also showing a measurement having a functioning temperature compensation, while curves 15, 16 each show an offset in the permittivity and accordingly a poorly functioning temperature compensation.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for testing a measuring device which ascertains a physical variable of a studied object, dependent at least on a temperature of the studied object, the method comprising:
    measuring the physical variable at at least two different temperatures of the studied object to obtain at least two different values of the physical variable; and
    determining a calibration status of the measuring device on the basis of a known temperature dependence of the physical variable and using the at least two different values of the physical variable measured at the at least two different temperatures.

2. The method as recited in claim 1, wherein the physical variable is measured multiple times during a heating or cooling process of the studied object.

3. The method as recited in claim 1, wherein the measurement of the physical variable is performed using a temperature compensation and a calibration status is determined from the difference of the temperatures and the difference of the measured values.

4. The method as recited in claim 1, wherein an actually existing value of the physical variable is assigned to the temperature dependence of the physical variable to be measured ascertained by measurement without temperature compensation, this actually existing value being compared to the measured value of the physical variable, and a signal is output upon the existence of a minimum deviation.

5. The method as recited in claim 1, wherein the temperature dependence of the physical variable is ascertained on the basis of measurements, the actual value of the physical variable of the studied object is known, and both the measurement of the physical variable and the consideration of the temperature dependence are calibrated on the basis of these data.

6. The method as recited in claim 1, wherein reference measurements of the physical variable are performed at two known values of the physical variable, and measurements of the temperature dependence occur at each of two different values of the physical variable, and a calibration in regard to the measurement of the physical variable and in regard to the consideration of the temperature dependence is subsequently performed on the basis of the acquired data.

7. The method as recited in claim 1, wherein an actually existing value of the physical variable is assigned to the temperature dependence of the physical variable to be measured ascertained by measurement without temperature compensation, this actually existing value being compared to the measured value of the physical variable, and a signal is output upon the existence of a minimum deviation,
    wherein the temperature dependence of the physical variable is ascertained on the basis of measurements, the actual value of the physical variable of the studied object is known, and both the measurement of the physical variable and the consideration of the temperature dependence are calibrated on the basis of these data, and
    wherein reference measurements of the physical variable are performed at two known values of the physical variable, and measurements of the temperature dependence occur at each of two different values of the physical variable, and a calibration in regard to the measurement of the physical variable and in regard to the consideration of the temperature dependence is subsequently performed on the basis of the acquired data.

8. A method for checking a measuring device, which ascertains a physical variable, dependent at least in part on a temperature of a studied object, the method comprising:
    measuring the physical variable at a known temperature and on two different studied objects, wherein, for each of the two different studied objects, the physical variable is known; and
    determining a calibration status of the measuring device on the basis of a temperature dependence of the physical variable known for different values of the physical variable.

9. The method as recited in claim 8, wherein the physical variable is the permittivity or a variable clearly connected thereto.

10. The method as recited in claim 8, wherein the studied object is a material whose permittivity may change.

11. The method as recited in claim 10, wherein the studied object is at least one of: a frying fat and a frying oil.

12. The method as recited in claim 8, wherein the physical variable is the permittivity or a variable clearly connected thereto, and wherein the studied object is a material whose permittivity may change.

13. A system for testing a measuring device, comprising:
    a sensor that measures at least two measured values of a physical variable of a material at at least two different temperatures;
    a memory that stores known temperature and physical variable information;
    an analysis module coupled to the sensor and the memory that determines a temperature dependency characteristic using the at least two measured values of the physical variable at the at least two different temperatures and analyzes the temperature dependency characteristic using the known temperature and physical variable information to obtain an analysis result, wherein the analysis module determines a calibration status of the measured device according to the analysis result.

14. The system according to claim 13, further comprising:
    a temperature sensor that measures a temperature of the material.

15. The system according to claim 13, further comprising:
    a temperature regulating unit that controls a temperature of the material.

16. The system according to claim 13, further comprising:
    a display coupled to the analysis module.

17. The system according to claim 16, wherein the analysis module outputs a signal to the display indicating the analysis result.

18. The system according to claim 13, wherein the analysis module calibrates the measured device according to the analysis result.

19. The system according to claim 13, wherein the material is at least one of: a frying oil and a frying fat.

20. The system according to claim 13, wherein the physical variable of the material is at least one of: a permittivity, a relative dielectric constant, an index of refraction, and a capacitance.

* * * * *